(12) United States Patent
Kloeppner et al.

(10) Patent No.: US 11,414,594 B2
(45) Date of Patent: Aug. 16, 2022

(54) LOW DIMERIZING VIOLOGEN ELECTROCHROMIC COMPOUNDS AND DEVICES

(71) Applicant: Gentex Corporation, Zeeland, MI (US)

(72) Inventors: Leroy J. Kloeppner, Jenison, MI (US); Zachary B. Erno, Hudsonville, MI (US); Henry A. Luten, Holland, MI (US)

(73) Assignee: GENTEX CORPORATION, Zeeland, MI (US)

( * ) Notice: Subject to any disclaimer, the term of this patent is extended or adjusted under 35 U.S.C. 154(b) by 395 days.

(21) Appl. No.: 16/841,966

(22) Filed: Apr. 7, 2020

(65) Prior Publication Data

US 2020/0326602 A1    Oct. 15, 2020

Related U.S. Application Data

(60) Provisional application No. 62/831,315, filed on Apr. 9, 2019.

(51) Int. Cl.
| | | |
|---|---|---|
| *C09K 9/02* | (2006.01) | |
| *C09K 9/00* | (2006.01) | |
| *C07D 471/04* | (2006.01) | |
| *C07D 471/14* | (2006.01) | |
| *C07F 9/576* | (2006.01) | |
| *C07F 9/6584* | (2006.01) | |
| *G02F 1/1516* | (2019.01) | |
| *G02F 1/1523* | (2019.01) | |

(52) U.S. Cl.
CPC ............ *C09K 9/02* (2013.01); *C07D 471/04* (2013.01); *C07D 471/14* (2013.01); *C07F 9/5765* (2013.01); *C07F 9/6584* (2013.01); *C09K 9/00* (2013.01); *G02F 1/1516* (2019.01); *C09K 2211/1044* (2013.01); *C09K 2211/1055* (2013.01); *G02F 1/1523* (2013.01)

(58) Field of Classification Search
None
See application file for complete search history.

(56) References Cited

U.S. PATENT DOCUMENTS

| | | |
|---|---|---|
| 4,902,108 A | 2/1990 | Byker |
| 5,818,625 A | 10/1998 | Forgette et al. |
| 5,928,572 A | 7/1999 | Tonar et al. |
| 5,940,201 A | 8/1999 | Ash et al. |
| 6,268,950 B1 | 7/2001 | Ash et al. |
| 6,445,486 B1 | 9/2002 | Lomprey et al. |
| 6,597,489 B1 | 7/2003 | Guarr et al. |
| 6,635,194 B2 | 10/2003 | Kloeppner et al. |
| 6,661,559 B2 | 12/2003 | Byker et al. |
| 6,700,692 B2 | 3/2004 | Tonar et al. |
| 7,001,540 B2 | 2/2006 | Kloeppner et al. |
| 9,964,828 B2 | 5/2018 | Theiste et al. |
| 10,040,763 B2 | 8/2018 | Lin et al. |
| 2008/0316574 A1 | 12/2008 | Baumann et al. |

FOREIGN PATENT DOCUMENTS

| | | |
|---|---|---|
| WO | 2017154681 A1 | 9/2017 |
| WO | 2018069516 A1 | 4/2018 |

OTHER PUBLICATIONS

Kawashima et al. "The Synthesis and Properties of a Methylviologen Analogue" Tetrahedron Letters, 1984, vol. 25, No. 15, pp. 1585-1586.*
Gill, E.W., The synthesis and characterization of some 2,7-diazaphenanthrene derivatives, Dep. Pharmacol, Oxford Univ., Oxford, UK, Journal of Heterocyclic Chemistry, 20(4), 1983, 1107-1109.

* cited by examiner

*Primary Examiner* — Joseph R Kosack
(74) *Attorney, Agent, or Firm* — Price Heneveld LLP; Brian James Brewer

(57) ABSTRACT

A low dimerizing electrochromic compound for use in electrochromic mediums and electro-optic elements incorporating said electrochromic mediums is provided. The low dimerizing electrochromic compound is represented by Formula (I):

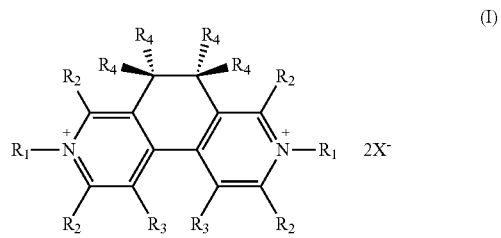

wherein each $R_1$ is individually an alkyl, a hydroxyalkyl, or an alkyl substituted with at least one polymerizable functional group; each $R_2$ is a hydrogen; each $R_3$ is individually a hydrogen or an alkyl; and each $R_4$ is individually a hydrogen, an alkyl, or a hydroxyalkyl; and $X^-$ is an anion.

17 Claims, 5 Drawing Sheets

Structure (I)

LOW DIMERIZING VIOLOGEN ELECTROCHROMIC COMPOUNDS AND DEVICES

CROSS-REFERENCE TO RELATED APPLICATIONS

This application claims priority to and the benefit under 35 U.S.C. § 119(e) of U.S. Provisional Application No. 62/831,315, filed on Apr. 9, 2019, entitled LOW DIMERIZING VIOLOGEN ELECTROCHROMIC COMPOUNDS AND DEVICES, the disclosure of which is hereby incorporated herein by reference in its entirety.

FIELD OF THE DISCLOSURE

The present disclosure generally relates to electrochromic compounds for electro-optic elements and mediums, and more particularly to low dimerizing viologen-based electrochromic compounds.

SUMMARY OF THE DISCLOSURE

According to one aspect of the present disclosure, an electro-optic element includes a low dimerizing electrochromic compound of Formula (I):

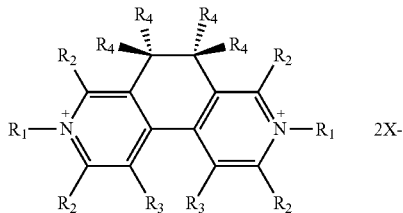

wherein each $R_1$ is individually an alkyl, a hydroxyalkyl, or an alkyl substituted with at least one polymerizable functional group; each $R_2$ is a hydrogen; each $R_3$ is individually a hydrogen or an alkyl; each $R_4$ is individually a hydrogen, an alkyl, or a hydroxyalkyl; and $X^-$ is an anion.

According to one aspect of the present disclosure, an electrochromic medium for use in an electro-optic element includes a low dimerizing electrochromic compound of Formula (I):

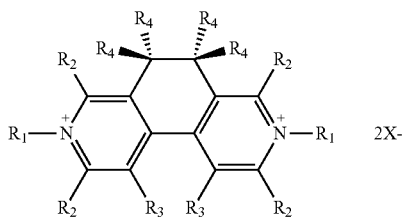

wherein each $R_1$ is individually an alkyl, a hydroxyalkyl, or an alkyl substituted with at least one polymerizable functional group; each $R_2$ is a hydrogen; each $R_3$ is individually a hydrogen or an alkyl; each $R_4$ is individually a hydrogen, an alkyl, or a hydroxyalkyl; and $X^-$ is an anion.

According to one aspect of the present disclosure, an electro-optic element includes a low dimerizing electrochromic compound of Formula (II):

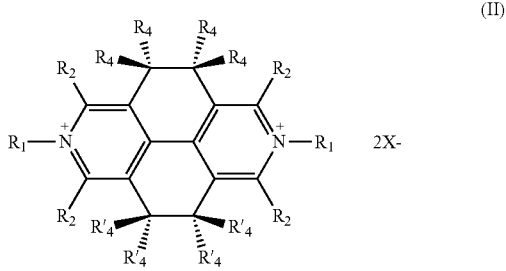

wherein each $R_1$ is individually an alkyl, a hydroxyalkyl, or an alkyl substituted with at least one polymerizable functional group; each $R_2$ is a hydrogen; each $R_4$ is individually a hydrogen, an alkyl, or a hydroxyalkyl; each $R'_4$ is individually a hydrogen, an alkyl, or a hydroxyalkyl; and $X^-$ is an anion.

According to one aspect of the present disclosure, an electrochromic medium for use in an electro-optic element includes a low dimerizing electrochromic compound of Formula (II):

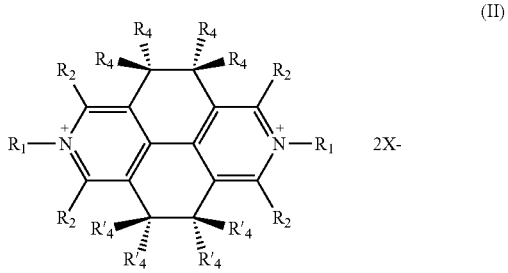

wherein each $R_1$ is individually an alkyl, a hydroxyalkyl, or an alkyl substituted with at least one polymerizable functional group; each $R_2$ is a hydrogen; each $R_4$ is individually a hydrogen, an alkyl, or a hydroxyalkyl; each $R'_4$ is individually a hydrogen, an alkyl, or a hydroxyalkyl; and $X^-$ is an anion.

These and other features, advantages, and objects of the present disclosure will be further understood and appreciated by those skilled in the art by reference to the following specification, claims, and appended drawings.

DETAILED DESCRIPTION

Figure 1:
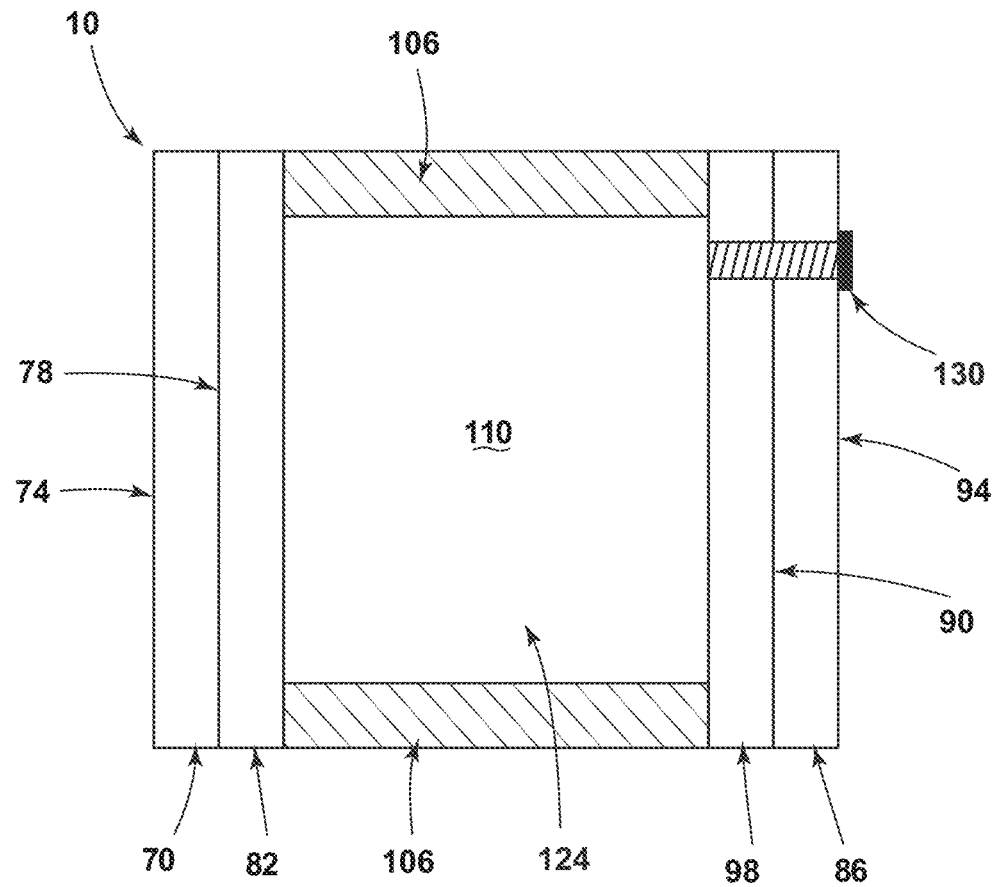
FIG. 1 is a cross-sectional schematic representation of an electrochromic device, according to an aspect of the present disclosure.

The present illustrated embodiments reside primarily in combinations of materials, method steps, and apparatus components relating to low dimerizing viologen-based compounds for use in electrochromic mediums and related devices. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

As used herein, the term "and/or," when used in a list of two or more items, means that any one of the listed items can be employed by itself, or any combination of two or more of the listed items, can be employed. For example, if a composition is described as containing components A, B, and/or C, the composition can contain A alone; B alone; C alone; A and B in combination; A and C in combination; B and C in combination; or A, B, and C in combination.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to the surface of the device closer to an intended viewer of the device, and the term "rear" shall refer to the surface of the device further from the intended viewer of the device. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Aspects of the present disclosure relate to a family of electrochromic compounds capable of attenuating the transmittance of at least a portion of the electromagnetic spectrum. The electrochromic compounds of the present disclosure can be used in electro-optic elements and electrochromic devices incorporating such electro-optic elements. The electrochromic compounds of the present disclosure include a low dimerizing viologen-based compound of Formula (I):

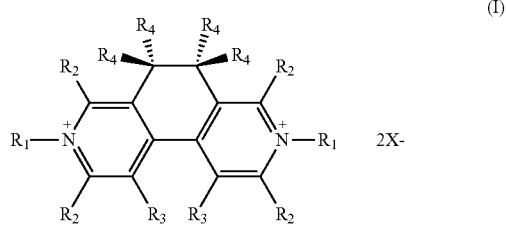

wherein each $R_1$ is individually an alkyl, a hydroxyalkyl, or an alkyl substituted with at least one polymerizable functional group; each $R_2$ is a hydrogen; each $R_3$ is individually a hydrogen or an alkyl; each $R_4$ is individually a hydrogen, an alkyl, or a hydroxyalkyl; and $X^-$ is an anion. The compounds of Formula (I) generally include a 3,3' ethylene bridge in which each $R_4$ may be a hydrogen, an alkyl, or a hydroxyalkyl.

According to another aspect of the present disclosure, the electrochromic compounds include a low dimerizing viologen-based compound of Formula (II):

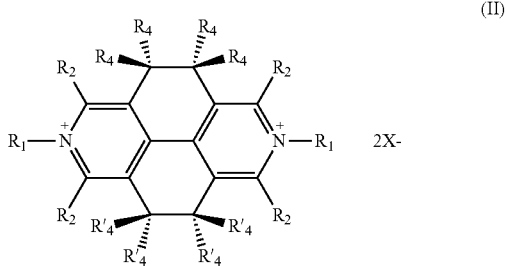

wherein each $R_1$ is individually an alkyl, a hydroxyalkyl, or an alkyl substituted with at least one polymerizable functional group; each $R_2$ is a hydrogen; each $R_4$ is individually a hydrogen, an alkyl, or a hydroxyalkyl; each $R'_4$ is individually a hydrogen, an alkyl, or a hydroxyalkyl; and $X^-$ is an anion. The compounds of Formula (II) are similar to the compounds of Formula (I) except that the compounds of Formula (II) also includes a 5,5' ethylene bridge in which each $R_4$ and $R'_4$ may be a hydrogen, an alkyl, or a hydroxyalkyl.

The viologen-based electrochromic compounds of Formula (I) and (II) can be used as a cathodic material in combination with an anodic material to form electro-optic elements that can be incorporated into electrochromic devices. The viologen-based electrochromic compounds of Formula (I) and (II) of the present disclosure can be characterized by low dimer formation when utilized in electro-optic elements and electrochromic devices. By way of introduction, a conventional electrochromic device can include a conventional viologen, such as di-n-octyl viologen bis(tetrafluoroborate) (also referred to as octyl viologen), and a conventional anodic material, such as 5,10-dihydro-5,10-dimethyl phenazine (DMP). In operation, the conventional electrochromic device can exhibit a color change when the conventional viologen compound, octyl viologen, undergoes a one electron reduction, which results in an increase in absorbance of light in the visible region of the electromagnetic spectrum. For example, octyl viologen in a propylene carbonate (PC) solvent exhibits a lambda-max at about 605 nm upon experiencing a one electron reduction, and thus becomes blue in appearance. However, a second absorbance can also be observed when octyl viologen experiences a one electron reduction that has been theorized to be the result of dimerization of two, single electron reduced viologen single cation radicals. This second absorbance can be blue shifted from the single cation radical absorbance, with the cation radical dimer exhibiting a lambda-max of about 520 nm. The additional absorbance exhibited by the viologen radical cation dimer can result in a shift in the appearance of the electrochromic device that may not be desirable.

Viologen dimer formation is typically a reversible process that is characterized by a dimer formation reaction rate (forward reaction rate) and a single cation radical formation reaction rate (reverse reaction rate), and thus the color shift due to dimer formation is also a reversible process. The dimer forward and reverse reaction rates can be affected by a variety of factors, such as temperature and cation radical concentration. Because the color shift is affected by the dimer forward and reverse reaction rates, these factors will also affect the color shift. For example, the temperature environment within which an electrochromic device is used may result in an increase in the dimer forward reaction rate (rate of dimer formation) compared to other end use environments, and thus the color shift due to dimer formation may be a greater challenge for some devices compared to others. The viologen-based compounds of Formulas (I) and (II) according to the present disclosure can exhibit a decreased or low dimerizing characteristic when used in an electro-optic element. The viologen-based compounds of the present disclosure can reduce or eliminate the color shift that some conventional electrochromic devices may experience as a result of dimerization of viologen-based cation radicals.

Referring to FIGS. 1 and 2A-E, reference numeral 10 generally designates an electrochromic device according to an aspect of the present disclosure. The electrochromic device 10 can include a first substrate 70 having a first surface 74 and a second surface 78, and a first electrically conductive layer 82 disposed on the second surface 78. A second substrate 86 is provided opposite the first substrate 70, and includes a third surface 90 and a fourth surface 94. A second electrically conductive layer 98 is disposed on the third surface 90. The first substrate 70 and the second substrate 86, along with a sealing member 106 define a chamber 110 for containing an electrochromic medium. The electrochromic device 10 can also include one or more plugs 130 associated with one or more fill ports. The one or more fill ports may be disposed within the first substrate 70, the second substrate 86, or the sealing member 106. Upon mounting as a mirror, window, filter, or other device, the electrochromic device 10 may optionally include a bezel (not shown) that extends around a periphery of at least one of the first substrate 70 and/or the second substrate 86 to conceal and/or protect components of the electrochromic device 10 and the like, such as a bus connector (if present), the sealing member 106, one or more plugs 130, and/or the one or more fill ports.

In some aspects, the first or second substrates 70, 86 may be larger than one another or the same in size, but shifted, to create an offset along at least a portion of the perimeter of the electrochromic device 10 to allow for easier access to the first and/or second electrically conductive layers 82, 98. The first and/or second substrates 70, 86 can be made of glass, plastic, or other optically transparent or translucent material, non-limiting examples of which include borosilicate glass, soda lime glass, or polymeric materials such as natural and synthetic polymeric resins, plastics, and/or composites including polyesters (e.g. PET), polyimides (PI), polycarbonates, polysulfones, polyethylene naphthalate (PEN), ethylene vinyl acetate (EVA), acrylate polymers, as well as cyclic olefin copolymers (COC) commercially available from TOPAS° Advanced Polymers. In some aspects, both the first and second substrates 70, 86 are made of an optically transparent or translucent material, while in other aspects, only the first substrate 70 is made of an optically transparent or translucent material. The first and second substrates 70, 86 can be made from the same or different materials and may have the same or different dimensions. According to some aspects, the second electrically conductive layer 98 may include a metal reflector or one or more coatings configured as a partially reflective, partially transmissive ("transflective") coating. Inclusion of a metal reflector or a transflective coating may render the electrochromic device 10 at least partially reflective.

The first and second electrically conductive layers 82, 98 can include one or more layers of an electrically conductive material disposed on the first and second substrates 70, 86, respectively. These layers serve as electrodes (i.e., the cathode and the anode) for the electrochromic device 10. The electrically conductive material(s) of the first and/or second electrically conductive layers 82, 98 may be any suitable material that includes one or more of the following features: (a) is substantially transparent to visible and/or IR light; (b) bonds reasonably well to the first and second substrates 70, 86; (c) maintains the bond to the first and second substrates 70, 86 when associated with a sealing member 106; (d) is generally resistant to corrosion from materials contained within the electrochromic device 10 or the atmosphere; and/or (e) exhibits minimal diffuse or specular reflectance as well as sufficient electrical conductance. Depending on the application, only one of the first and second electrically conductive layers 82, 98 may be required to be transparent while the other electrically conductive layer 82, 98 may be opaque. In some applications, both the first and the second electrically conductive layers 82, 98 may be transparent. The electrically conductive material(s) forming the first and second electrically conductive layers 82, 98 may be the same or different. Non-limiting examples of electrically conductive material that may be used to form the first and/or second electrically conductive layers 82, 98 can include fluorine doped tin oxide (FTO), for example TECTM glass, indium/tin oxide (ITO), doped zinc oxide, indium zinc oxide (IZO), aluminum doped zinc oxide (AZO), and metal oxide/metal/metal oxide (wherein metal oxide can be substituted with metal carbide, metal nitride, metal sulfide, etc . . . ).

While aspects of the present disclosure are described in the context of the electrochromic device 10, aspects of the present disclosure may also be utilized in the context of other electrochromic devices, non-limiting examples of which include those disclosed in U.S. Pat. No. 5,818,625, issued Oct. 6, 1998 and entitled "Electrochromic Rearview Mirror Incorporating a Third Surface Metal Reflector,"; U.S. Pat. No. 6,597,489, issued Jul. 22, 2003 and entitled "Electrode Design for Electrochromic Devices,"; and U.S. Pat. No. 6,700,692, issued Mar. 2, 2004 and entitled "Electrochromic Rearview Mirror Assembly Incorporating a Display/Signal Light," all of which are incorporated herein by reference in their entirety including all references incorporated therein.

Still referring to FIGS. 1 and 2A-E, the electrochromic device 10 includes an electro-optic element 140 that is at least partially defined by the first and second substrates 70, 86, the chamber 110, and the electrochromic medium 124. The electro-optic element 140 allows the electrochromic device 10 to be operable between a transparent or clear state, which allows light having a wavelength within a predetermined wavelength range to pass through, and a darkened state, in which a portion, or no light having a wavelength within a predetermined wavelength range, is transmitted through the electro-optic element 140 (i.e., the electro-optic element 140 becomes essentially opaque or partially opaque to light having a wavelength within the predetermined wavelength range). The electro-optic element 140 may be operable between a substantially clear state and a substantially dark or darkened state, as well as intermediate states thereto. The darkened state of the electro-optic element 140 can be defined relative to the transmissivity of the substantially clear state. According to an aspect of the present disclosure, the transmissivity of the electro-optic element 140 in the substantially transparent or clear state may be greater than about 15%, greater than about 25%, greater than about 50%, greater than about 55%, or greater than about 85%. The percentage of reflectance, transmittance, and absorbance of the electro-optic element 140 sum to 100%. In some aspects, the transmissivity of the electro-optic element 140 in the substantially darkened state may be less than about 10% less than about 1%, less than about 0.1%, less than about 0.01%, or less than about 0.001%.

The seal 106 can traverse an approximate perimeter of, and is configured to cooperate with, the first and second substrates 70, 86 to define the chamber 110 as substantially hermetic. The seal 106 may be applied to the first or second substrates 70, 86 by methods commonly used in the liquid crystal display (LCD) industry, such as by silk-screening or dispensing. In one example, the seal 106 may incorporate a first and a second seal as components of the seal 106. In one example, first and second annular bands of highly conductive material are optionally deposited around the perimeter of the first and second substrates 70, 86, respectively, and electrically-conducting structures (e.g., clips or wires) are secured to the highly conductive material and spatially separated from one another. The electrically-conducting structures may supply an electrical voltage to the first and second annular bands of highly conductive material to create a voltage across the electro-optic element 140, thereby reversibly driving the electro-optic element 140 between the substantially dark and substantially clear states. The first and second annular bands of highly conductive material may include silver, gold, copper, or aluminum (such as, for example, in a form of metallic flakes or particles dispersed in a hosting material).

Referring to FIGS. 2A-E, the electro-optic element 140 includes an electrochromic medium, at least one cathodic component, and at least one anodic component. The anodic and cathodic components may alternatively be referred to as chromophores or electrochromic molecules. According to some aspects of the present disclosure, the anodic and/or cathodic components may be a polymer and/or a monomer. In some aspects, both the cathodic and anodic components are electroactive and at least one of them is electrochromic. It will be understood that regardless of its ordinary meaning, the term "electroactive" may mean a material that undergoes a modification in its oxidation state upon exposure to a particular electrical potential difference. Additionally, it will be understood that the term "electrochromic" may mean, regardless of its ordinary meaning, a material that exhibits a change in its extinction coefficient at one or more wavelengths upon exposure to a particular electrical potential difference. Electrochromic components, as described herein, include materials whose color or opacity are affected by an electrical current, such that when an electrical field is applied to the material, the color or opacity changes from a first state to a second state.

According to an aspect of the present disclosure, the cathodic component comprises a viologen-based compound of Formula (I):

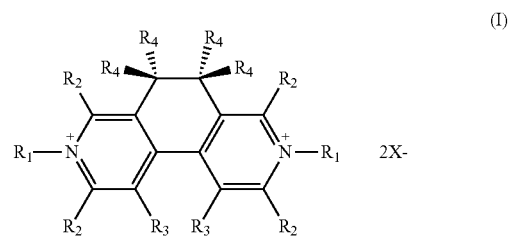

wherein each $R_1$ is individually an alkyl, a hydroxyalkyl, or an alkyl substituted with at least one polymerizable functional group; each $R_2$ is a hydrogen; each $R_3$ is individually a hydrogen or an alkyl; each $R_4$ is individually a hydrogen, an alkyl, or a hydroxyalkyl; and $X^-$ is an anion. The compounds of Formula (I) generally include a 3,3' ethylene bridge in which each $R_4$ may be a hydrogen, an alkyl, or a hydroxyalkyl. The viologen-based compound of Formula (I) can be characterized by a low rate of dimer formation or the absence of dimer formation.

As used herein, "alkyl" groups include straight chain and branched alkyl groups having from 1 to 20 carbon atoms, from 1 to 12 carbon atoms, from 1 to 8 carbon atoms, from 1 to 6 carbon atoms, from 6 to 20 carbon atoms, from 6 to 12 carbon atoms, from 8 to 20 carbon atoms, or from 12 to 20 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Non-limiting examples of branched alkyl groups include isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some aspects, haloalkyl refers to a per-haloalkyl group. As used herein, $C_m$-$C_n$, such as $C_1$-$C_{12}$, $C_1$-$C_8$, or $C_1$-$C_6$, when used before a group refers to that group containing m to n carbon atoms.

As used herein, "substituted" refers to an alkyl group in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some aspects, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides;

hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. Such substitution includes solubility enhancing groups as described in U.S. Pat. No. 6,445,486, issued Sep. 3, 2002.

Cycloalkyl groups are cyclic alkyl groups such as, but not limited to, cyclopropyl, cyclobutyl, cyclopentyl, cyclohexyl, cycloheptyl, and cyclooctyl groups. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings, non-limiting examples of which include decalinyl. Cycloalkyl groups also include rings that are substituted with straight or branched chain alkyl groups as defined above. Representative substituted cycloalkyl groups may be mono-substituted or substituted more than once, non-limiting examples of which include: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Non-limiting examples of suitable polymerizable functional groups include a vinyl group, an acrylate group, a methacrylate group, a vinyl ether group, a hydroxyl group, an isocyanate group, an oxetane group, and an epoxy group. According to one aspect, each $R_1$ individually can be a $C_1$-$C_{20}$ alkyl group including at least one substituted polymerizable functional group. In one aspect, the substituted alkyl group can include from 1 to 20 carbon atoms, from 1 to 12 carbon atoms, from 1 to 8 carbon atoms, from 1 to 6 carbon atoms, from 6 to 20 carbon atoms, from 6 to 12 carbon atoms, from 8 to 20 carbon atoms, or from 12 to 20 carbon atoms.

Non-limiting examples of the anion X include a halide, a borate, a fluoroborate, a tetraaryl borate, a hexafluoro metal or metalloid, a sulfate, a sulfonate, a sulfonamide, a carboxylate, a perchlorate, and a tetrachloroferrate. Additional non-limiting examples of suitable anions X include: $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CN)_2^-$, $N(CF_3SO_2)_2^-$, $C(CF_3SO_2)_3^-$, $N(SO_2C_2F_5)_2^-$, $Al(OC(CF_3)_3)_4^-$ or $BAr_4^-$, wherein Ar is a aryl or fluorinated aryl group. In one aspect, $X^-$ is $BAr_4^-$ and Ar is a pentafluorophenyl group. In another aspect, X is a tetrafluoroborate or a bis(trifluoromethylsulfonyl) imide anion. When shown in any compound herein, multiple X's may be a single anion or a mixture of two or more such anions.

Figure 3:
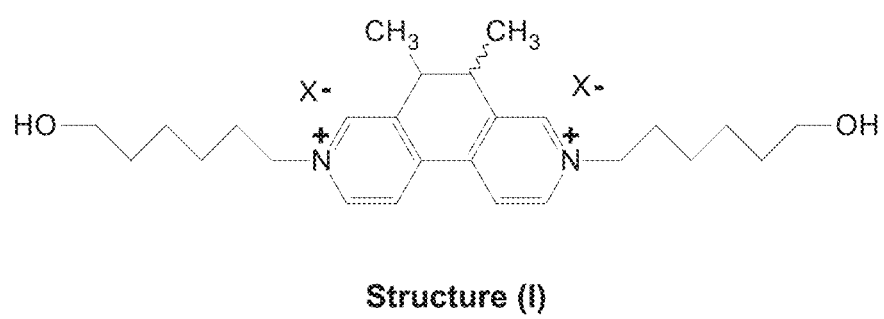
FIG. 3 illustrates the chemical structure of an exemplary electrochromic compound, Example Compound (I) according to an aspect of the present disclosure.

FIG. 3 illustrates an exemplary viologen-based compound (Example Compound (I)) according to Formula (I), according to an aspect of the present disclosure, characterized by a low or absent rate of dimer formation. In the example of Example Compound (I), each $R_1$ of Formula (I) is a $C_6$ alkyl group including a hydroxy substituent, each $R_2$ and $R_3$ are a hydrogen, and $R_4$ is a hydrogen or an alkyl group, and each $X^-$ is anion. According to one aspect, the length of the carbon chain of the alkyl can be selected to be from 1 to 20 carbon atoms, from 1 to 12 carbon atoms, from 1 to 8 carbon atoms, from 1 to 6 carbon atoms, from 6 to 20 carbon atoms, from 6 to 12 carbon atoms, from 8 to 20 carbon atoms, or from 12 to 20 carbon atoms.

According to another aspect of the present disclosure, the electrochromic compounds include a viologen-based compound of Formula (II):

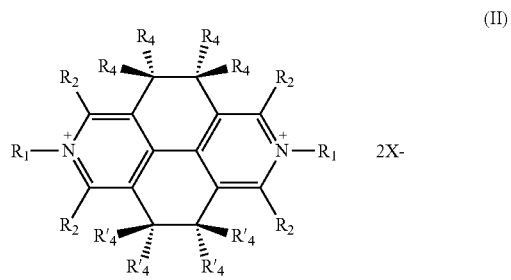

wherein each $R_1$ is individually an alkyl, a hydroxyalkyl, or an alkyl substituted with at least one polymerizable functional group; each $R_2$ is a hydrogen; each $R_4$ is individually a hydrogen, an alkyl, or a hydroxyalkyl; each $R'_4$ is individually a hydrogen, an alkyl, or a hydroxyalkyl; and X is an anion. The compounds of Formula (II) are similar to the compounds of Formula (I) except that the compounds of Formula (II) also include an 5,5' ethylene bridge in which $R_4$ and $R'_4$ may be a hydrogen, an alkyl, or a hydroxyalkyl. $R_1$ can be selected from any of the materials described herein with respect to $R_1$ of Formula (I). $R_4$ and $R'_4$ can be selected from any of the materials described herein with respect to $R_4$ of Formula (I). The viologen-based compound of Formula (II) can be characterized by a low or absent rate of dimer formation.

The present viologen-based compounds of Formula (I) and (II) can be utilized in solution form, gel form, or film form as the cathodic component in an electrochromic medium of an electro-optic element. The electrochromic medium may include layers of materials attached directly to an electrically conductive layer or confined in close proximity to an electrically conductive layer which remains attached or confined when components thereof are oxidized and/or reduced.

In one aspect, the viologen-based compounds of Formula (I) and (II) may be incorporated into a polymeric film to form a cathodic film. The present viologen-based compounds can be incorporated into the backbone of the polymeric chains forming the polymeric film and/or covalently bonded to the polymeric chains as pendant groups. For example, the cathodic film may be a polymeric film including a plurality of polymeric chains composed of a number of repeating monomer units forming a backbone of the polymer chains. In specific examples, the cathodic film may include a 4,4' bipyridine and 1,4 dibromobutane tetrafluroborate copolymer, a 4,4'-bipyridine and triethylene glycol tosylate copolymer and/or 4,4'-bipyridine and tetraethylene glycol tosylate copolymer, wherein at least a portion of the 4,4' bipyridine may include a 3,3'-ethylene and/or 5,5'-ethylene bridge, according to Formula (I) or (II). The cathodic film may include a binder polymer (e.g., polymethylmethacrylate (PMMA), polyvinyl formal, or polyethylene glycol), a plasticizer that will help facilitate ion conductivity (e.g., propylene carbonate or gamma-butyrolactone) and a supporting electrolyte salt (e.g., tetraethylammonium tetrafluoroborate or lithium hexafluorophosphate). The viologen-based compounds of Formula (I) and (II) may form pendant groups attached to the polymer backbone or be disposed between the monomer units of the backbone.

In another aspect, the cathodic film may be a solid polymer or a gel polymer. For example, the polymer may be an acrylate-based polymer that is dissolved in a solvent which incorporates the viologen-based compounds of Formula (I) or (II). This solution is then coated on the conductive surface of a substrate, followed by removal of the solvent. The resultant film is an acrylate film that may be hard or tacky to the touch. In another example, the polymer film may be a gel that contains solvent as well as the viologen-based compounds of Formula (I) or (II). Optionally, the polymer film maybe subsequently cross-linked for increased mechanical stability. Other non-limiting examples of polymer matrix systems that could be used with the viologen-based compounds of Formula (I) and (II) include: polyacrylate, polymethacrylates, polyethers, polyesters, polycarbonates, polyurethanes, polysiloxanes, polysilanes, polyacrylonitriles, polystyrenes, polymethacrylonitriles, polyamides, polyimides, polyvinylidene halides, and copolymers, or combinations of any two or more thereof. Further examples of polymer matrix materials used in electrochromic devices can be found in U.S. Pat. Nos. 6,635,194; 5,940,201; 5,928,572; and 9,964,828, which are herein incorporated by reference in their entirety.

According to one aspect, the viologen-based compounds of Formula (I) and (II) can include a hydroxyl group, such that the compound may be bound into a polymer matrix via a condensation reaction or react with an isocyanate functionality to form a polyurethane-based polymer matrix. Amines may also react with isocyanate functionalities to form urea and biuret linkages. It is also within the scope of the present disclosure to utilize other polymeric matrix systems that contain compounds of Formula (I) and/or Formula (II) that can be formed using a multi-functional epoxy in combination with a curing agent like an amine, alcohol, or anhydride or through base or acid catalyzed homo-polymerization. Non-limiting examples of materials that may be used as a polymeric matrix for covalently bonding with the viologen-based compounds of Formula (I) and (II) include: polymethylmethacrylate, polymethacrylate, polypropylene methacrylate, polystyrene, polyurethanes, polyethers, polyesters, polycarbonates, polysiloxanes, polysilanes, polyacrylonitriles, polymethacrylonitriles, polyamides, polyimides, polyvinylidene halides, and co-polymer and combinations of thereof. Further examples of polymer matrix materials can be found in U.S. Pat. Nos. 6,635,194; 5,940,201; 5,928,572; and 9,964,828, which are herein incorporated by reference in their entirety.

The anodic component of the electrochromic medium can be any suitable solvent, film, or gel-based material having an anodic component incorporated therein capable of cooperating with the viologen-based compounds of Formula (I) and (II) to form an electro-optic element. The anodic component can include an oxidizable compound, non-limiting examples of which include: metallocenes, 5,10-dihydrophenazines, phenothiazines, phenoxazines, carbazoles, triphenodithiazines, triphendioxazines, ferrocene, substituted ferrocenes, substituted ferrocenyl salts, phenazine, substituted phenazines, phenothiazine, substituted phenothiazines, including substituted dithiazines, thianthrene and substituted thianthrenes, di-tert-butyl-diethylferrocene, 5,10-dimethyl-5,10-dihydrophenazine (DMP), 3,7,10-trimethylphenothiazine, 2,3,7,8-tetramethoxy-thianthrene, 10-methylphenothiazine, tetra methylphenazine (TMP), bis(butyltriethylammonium)-para-methoxytriphenodithiazine (TPDT), 5,10-bis(3-hydroxypropyldimethylammoniumbutyl)-5,10-dihydrophenazine bis(hexafluorophosphate), and 3,10-dimethoxy-7,14-(triethylammoniumbutyl)-triphenodithiazinebis(tetrafluoroborate).

In some aspects, the anodic component can include a polymer film, such as polyaniline, polythiophenes, polymeric metallocenes, or a solid transition metal oxide, including, but not limited to, oxides of vanadium, nickel, and iridium. In another aspect, the anodic component includes a substituted or unsubstituted phenazine compound. For example, the anodic component can include a substituted or unsubstituted 2,7-dialkyl-5,10-dialkyl-5,10-dihydrophenazine compound. In another example, at least one alkyl group of the 5,10-dialkyl groups attached to the phenazine compound includes at least 4 carbon atoms and is void of any 3 hydrogen atoms, and at least one alkyl group of the 2,7-dialkyl groups attached to the phenazine compound includes at least 4 carbons. In another example, at least one alkyl group of the 5,10-dialkyl groups attached to the phenazine compound includes a substituted or unsubstituted neopentyl group, and at least one alkyl group of the 2,7-dialkyl groups attached to the phenazine compound includes a substituted or unsubstituted isopropyl, isobutyl, (2-ethylbutyl), or (2-propylpentyl) group. In another example, at least one alkyl group of the 5,10-dialkyl groups attached to the phenazine compound includes a neopentyl group, and at least one alkyl group of the 2,7-dialkyl groups attached to the phenazine compound includes a 2-ethyl-1-butanol group. In yet another example, at least one alkyl group of the 5,10-dialkyl groups attached to the phenazine compound includes a neopentyl group, and at least one alkyl group of the 2,7-dialkyl groups attached to the phenazine compound includes an isobutyl group.

According to some aspects, a concentration of the viologen-based compounds of Formula (I) and (II) and/or the anodic component in the electrochromic medium are from about 1 millimolar (mM) to about 500 mM, from about 2 mM to about 100 mM, about 5 mM to about 50 mM, about 40 mM to about 50 mM, about 60 mM to about 90 mM, or about 70 mM to about 80 mM. In one aspect, a concentration of the viologen-based compounds of Formula (I) and (11) is about 50 mM, about 50 mM to about 100 mM, about 60 to about 90 mM, or about 70 mM to about 80 mM. In one aspect, a concentration of the anodic component is at least 5 mM or about 2 mM to about 100 mM, about 5 mM to about 50 mM, or about 7 mM to about 50 mM.

The electrochromic medium may also include an electrolyte, which may be in the form of a solvent and a salt. The salt may be a metal salt or an ammonium salt. Non-limiting examples of suitable solvents for use in the electrolyte include: 3-methylsulfolane, dimethyl sulfoxide, dimethyl formamide, tetraglyme, and other polyethers; alcohols such as ethoxyethanol; nitriles, such as acetonitrile, glutaronitrile, 3-hydroxypropionitrile, and 2-methylglutaronitrile; ketones including 2-acetylbutyrolactone, and cyclopentanone; cyclic esters including beta-propiolactone, gamma-butyrolactone, and gamma-valerolactone; propylene carbonate (PC), ethylene carbonate; and homogenous mixtures thereof. Non-limiting examples of suitable salts include: metal or ammonium salts, such as $Li^+$, $Na^+$, $K^+$, $NR'_4^+$ (where each R' is individually H, alkyl, or cycloalkyl), of the following anions $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CF_3SO_2)_2^-$, $C(CF_3SO_2)_3^-$, $N(SO_2C_2F_5)^-$, $Al(OC(CF_3)_3)_4^-$, or $BAr_4^-$, wherein Ar is an aryl or fluorinated aryl group such as, but not limited to, $C_6H_5$, $3,5-(CF_3)_2C_6H_3]_4$, or $C_6F_5$.

The electrochromic medium may optionally include additional materials, such as light absorbers, light stabilizers, thermal stabilizers, antioxidants, oxygen scavengers, thickeners, viscosity modifiers, tint providing agents, redox buffers, and mixtures of any two or more such materials. Non-limiting examples of UV-stabilizers may include ethyl-2-cyano-3,3-diphenyl acrylate; (2-ethyl hexyl)-2-cyano-3,3-diphenyl acrylate; 2-(2'-hydroxy-4'-methylphenyl)benzotriazole, sold by Ciba-Geigy Corp. under the trademark Tinuvin® P; 3-[3-(2H-benzotriazole-2-yl)-5 -(1,1-dimethylethyl)-4-hydroxyphenyl]propionic acid pentyl ester prepared from Tinuvin® 213, sold by Ciba-Geigy Corp., via conventional hydrolysis followed by conventional esterification (hereinafter "Tinuvin® PE"); 2,4-dihydroxybenzophenone; 2 -hydroxy-4-methoxybenzophenone; and 2-ethyl-2'-ethoxyalanilide.

Figure 2A:
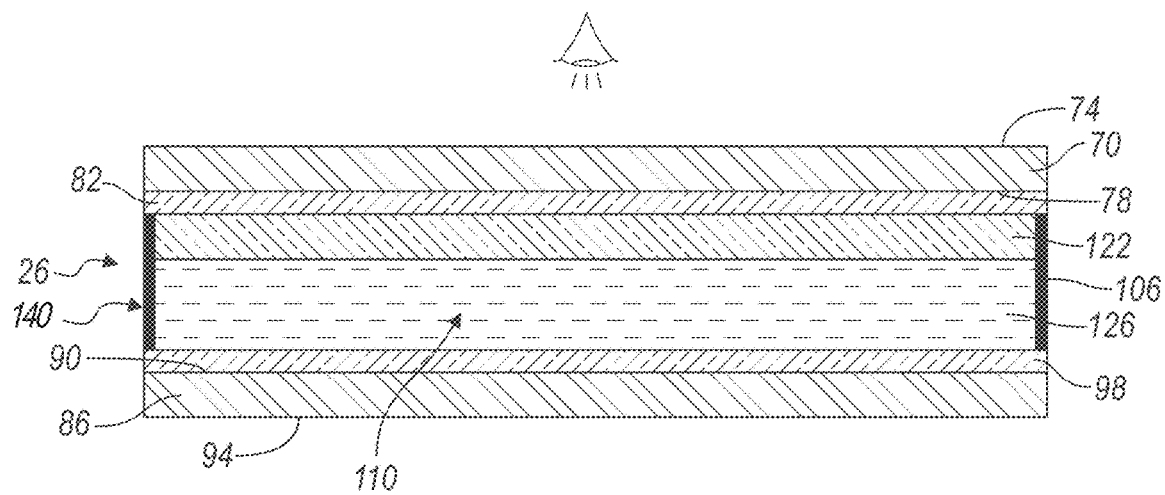
FIG. 2A is a cross-sectional view of an electro-optic element, according to an aspect of the present disclosure.
Figure 2B:
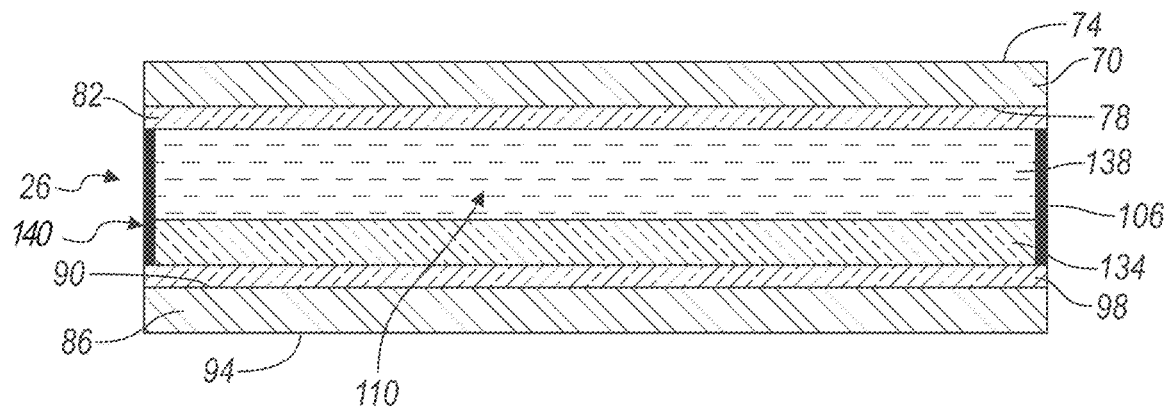
FIG. 2B is a cross-sectional view of an electro-optic element, according to an aspect of the present disclosure.
Figure 2C:
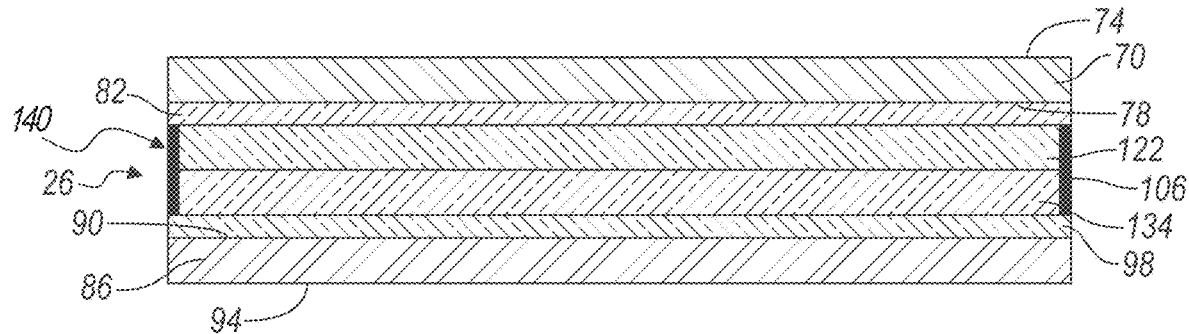
FIG. 2C is a cross-sectional view of an electro-optic element, according to an aspect of the present disclosure.
Figure 2D:
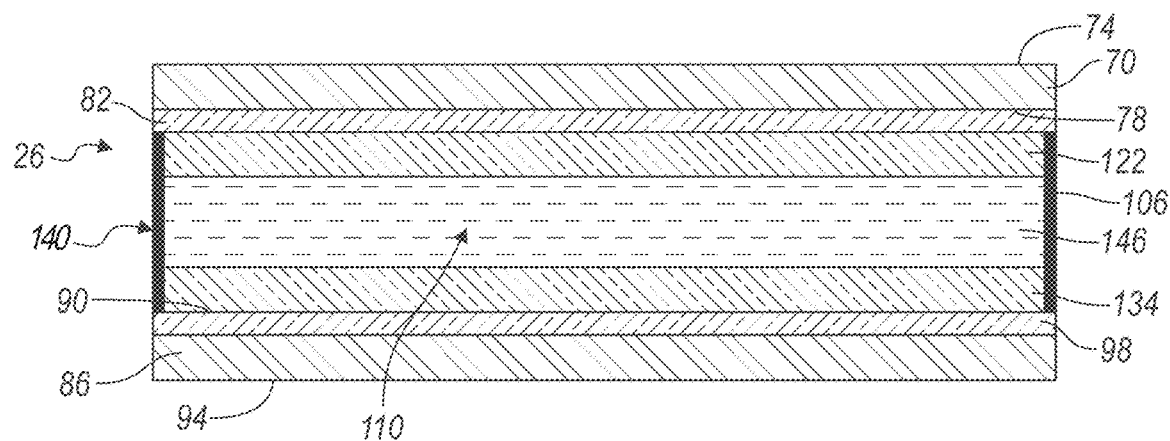
FIG. 2D is a cross-sectional view of an electro-optic element, according to an aspect of the present disclosure.

FIGS. 2A, 2C, and 2D illustrate exemplary configurations of the electro-optic element 140 including a cathodic film 122 including the low dimerizing viologen-based compounds of Formula (I) or (II) according to an aspect of the present disclosure, wherein at least a portion of the compounds of Formula (I) and/or Formula (II) are covalently bound into the film. As illustrated in FIG. 2A, the cathodic film 122 can be utilized in an electro-optic element 140 in combination with an anodic solution or gel 126. The cathodic film 122 can be disposed on the first electrically conductive layer 82 while the anodic solution or gel 126 can be disposed on the second electrically conductive layer 98. Optionally, the relative locations of the cathodic film 122 and the anodic solution or gel 126 can be reversed. The anodic solution or gel 126 can be an electrochromic solution or gel incorporating any suitable anodic component. Non-limiting examples of suitable electrochromic gels can be found in U.S. Pat. No. 6,268,950 entitled "Electrochromic Mirror with Two Thin Glass Elements and a Gelled Electrochromic Medium," and U.S. Pat. No. 7,001,540 entitled "Electrochromic Medium having a Self-healing Cross-linked Polymer Gel and Associated Electrochromic Device," both of which are hereby incorporated by reference in their entirety.

Additionally, the anodic solution or gel 126 may contain one or more electrolytes configured to facilitate electrical communication of the first and second electrically conductive layers 82, 98 across the anodic solution or gel 126 and cathodic film 122. The anodic solution or gel 126 may be in a semi-liquid state capable of transporting the anodic component to the cathodic component within the cathodic film 122. For example, the anodic solution or gel 126 may permeate the cathodic film 122 with the one or more electrolyte salts and/or anodic components. In the depicted example, either or both of the cathodic and anodic components of the cathodic film 122 and anodic solution or gel 126, respectively, may be electrochromic.

FIG. 2B illustrates an exemplary configuration of the electro-optic element 140 including a cathodic solution or gel 138 including the low dimerizing viologen-based compounds of Formula (I) or (II) according to an aspect of the present disclosure. As illustrated in FIG. 2B, the cathodic solution or gel 138 can be utilized in the electro-optic element 140 with the anodic film 134 of FIGS. 2B-D. The cathodic solution or gel 138 can be disposed on the first electrically conductive layer 82, while the anodic film 134 can be disposed on the second electrically conductive layer 98, or vice versa. The cathodic solution or gel 138 can be an electrochromic gel that may contain one or more electrolytes configured to facilitate electrical communication of the first and second electrically conductive layers 82, 98 across the cathodic solution or gel 138 and anodic film 134. According to one aspect, the cathodic solution or gel 138 may be in a semi-liquid state capable of transporting the cathodic component to the anodic component within the anodic film 134. For example, the cathodic solution or gel 138 may permeate the anodic film 134 with the one or more electrolyte salts and/or cathodic components. In the depicted example, either or both of the anodic and cathodic components of the anodic film 134 and cathodic solution or gel 138, respectively, may be electrochromic.

The anodic film 134 can be any suitable film incorporating the anodic component therein.

For example, the anodic film 134 may be a polymeric film including a plurality of polymeric chains composed of a number of repeating monomer units forming a backbone of the polymer chains. In some examples, the backbone of the polymer chains may have one or more pendant groups extending therefrom. In one example, the anodic film 134 may include 2,7-bis(2-hydroxyethyl)-5,10 hydro-5,10-bis (neopentyl)phenazine and tolylene-2,4-diisocyanate copolymer. The anodic film 134 may include a binder polymer (e.g., polymethylmethacrylate (PMMA), polyvinyl formal, or polyethylene glycol), a plasticizer that will help facilitate ion conductivity (e.g., propylene carbonate or gamma-butyrolactone) and a supporting electrolyte salt (e.g., tetraethylammonium tetrafluoroborate or lithium hexafluorophosphate). In examples of the of the electro-optic structure 114 including the anodic film 134, the anodic component may be disposed between the monomer units of the backbone. In other examples, the pendant groups may additionally or alternatively include the anodic component.

Referring now to the example depicted in FIG. 2C, the electro-optic element 140 includes both the cathodic film 122 and the anodic film 134. The cathodic film 122 and the anodic film 134 may be in direct contact with one another, or may be separated (e.g., by a film which is configured to promote electrical or ion exchange). As explained above, the cathodic and anodic films 122, 134 may be polymeric films including the cathodic component and anodic component disposed along the backbone, or on pendants, of the polymeric chains of the cathodic and anodic films 122, 134, respectively.

Referring now to the example depicted in FIG. 2D, the electro-optic element 140 includes both the cathodic film 122 and the anodic film 134 in addition to an electrolyte layer 146 separating the films 122, 134. The electrolyte layer 146 may be a gel (e.g., a semi-liquid configured to permeate the cathodic and anodic films 122, 134) or polymeric electrolyte. In examples utilizing a polymeric electrolyte as the electrolyte layer 146, the polymeric electrolyte may include poly(styrene-ran-ethylene), polystyrene-block-poly(ethylene-ran-butylene), poly(styrene-ran-ethylene), polystyrene-block-poly(ethylene/butylene)-block-polystyrene, poly(ethylene glycol), poly(methyl methacrylate), other polymer electrolytes and/or combinations thereof. The electrolyte layer 146 may partially permeate the cathodic and anodic films 122, 134.

Figure 2E:
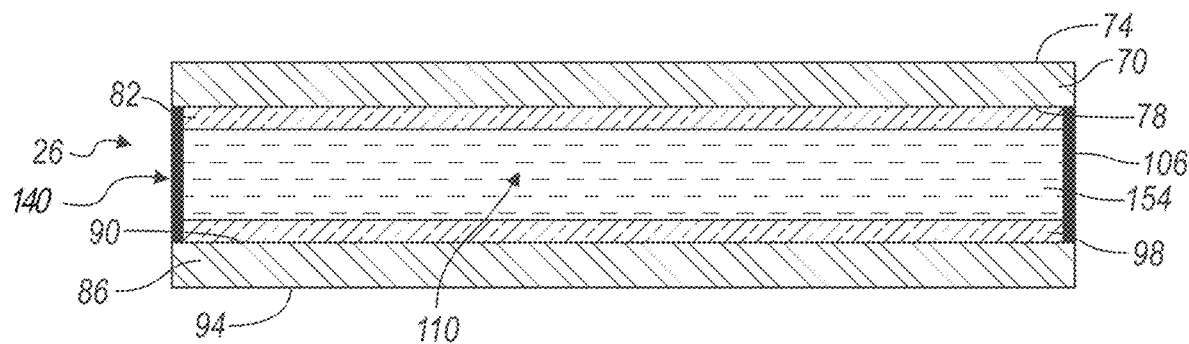
FIG. 2E is a cross-sectional view of an electro-optic element, according to an aspect of the present disclosure.

Referring now to the example depicted in FIG. 2E, the electro-optic element 140 may include an electro-optic film 154. The electro-optic film 154 may be a polymeric material composed of a plurality of polymeric chains, similar to the cathodic and anodic films 122, 134 (FIGS. 2C and 2D). In such an example, the electro-optic film 154 may contain both the anodic component and the cathodic component on the backbones of the polymeric chains, and/or as pendant groups. In some examples, the anodic component and cathodic component may both be positioned on the same polymer chains, while in other examples, the anodic component and cathodic component may be positioned on separate polymeric chains. Alternatively, the electro-optic film 154 may be a solution or a gel that contains both anodic and cathodic materials not bound to a polymer, but free to diffuse through the electro-optic film 154.

Conventional electro-optic elements that utilize viologens that exhibit dimerizing behavior can experience a shift in the observed color appearance based on the formation of the viologen dimers. The color shift observed as a result of viologen dimerizing can be effected by a variety of factors, examples of which include temperature, concentration of the viologen reduced radical, the electrical potential applied to the electrochromic device, the choice of solvent, and/or the choice of plasticizer. For example, temperature can affect the degree of dimerization, with lower temperatures often producing higher dimerization rates. Higher concentrations and electrical potentials can also increase the rate of dimer formation. In addition, conditions which restrict movement of the viologen, such as incorporation into a film or cross-linking, can increase dimerization.

The viologen-based compounds of Formula (I) and (II) of the present disclosure include features that can decrease the rate of dimer formation, and in particular may decrease the rate of dimer formation under the conditions typically experienced by electrochromic devices such as mirrors and windows and the like. The viologen-based compounds of Formula (I) and (II) of the present disclosure include structural components in the form of one or two ethylene bridges, respectively, which have been found to decrease the rate of dimer formation. The viologen-based compounds of Formula (I) and (II) of the present disclosure can be used to decrease color variation in electrochromic devices due to dimerization and may also result in faster clearing rates of the electrochromic devices compared to devices which exhibit a higher rate of dimer formation. In some scenarios, conventional viologen dimers may decrease the coloring and clearing rates of the electrochromic devices as compared to the single viologen. The viologen-based compounds of Formula (I) and (II) of the present disclosure exhibit a lower rate of dimer formation and thus are less likely to form dimers which could slow the rate of coloring and clearing in an electrochromic device.

The viologen-based compounds of Formula (I) and (II) of the present disclosure may be utilized in electrochromic mediums for electro-optic elements that may be utilized in a variety of different electrochromic devices, non-limiting examples of which include interior and exterior mirror assemblies, interior and exterior windows, sun roofs, heads-up displays, display screens, filter assemblies, eye wear, cameras, and display boards.

The following examples describe various features and advantages provided by the disclosure, and are in no way intended to limit the invention and appended claims.

EXAMPLES

Example 1

Figure 4:
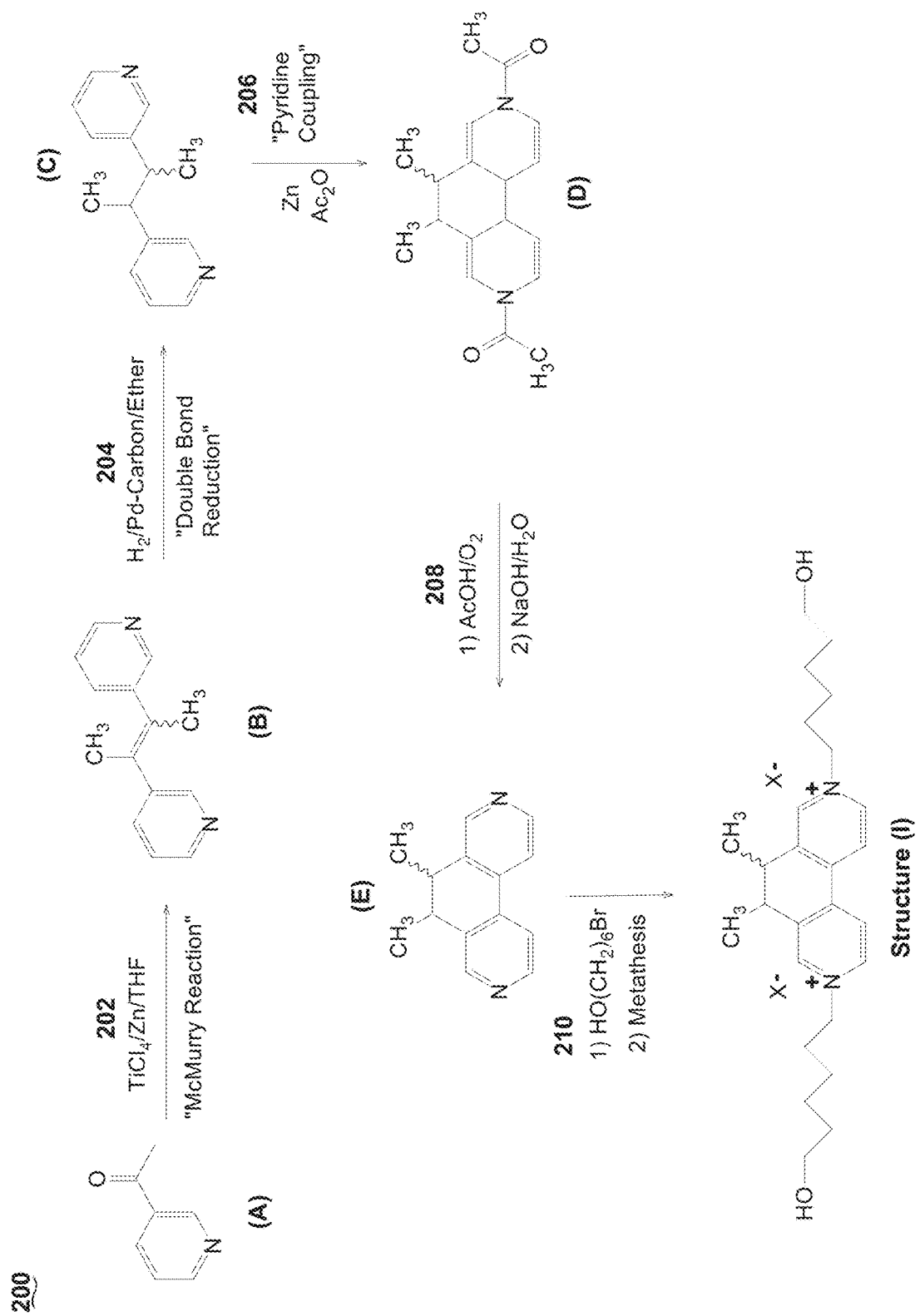
FIG. 4 is a flow chart depicting a synthetic scheme for synthesizing an exemplary electrochromic compound, according to an aspect of the present disclosure.

FIG. 4 illustrates an exemplary synthetic scheme 200 for synthesizing the low-dimerizing viologen-based compound of Example Compound (I). While the synthesis is discussed in the context of Example Compound (I), it is understood that the synthesis process is applicable to other low-dimerizing viologen-based compounds of Formulas (I) and (II). It is also understood that the compound of Example Compound (I) may be synthesized according to other processes. It is also understood that synthetic scheme 200 may include additional or alternative steps without deviating from the scope of the present disclosure.

Still referring to FIG. 4, step 202 is a reductive coupling step in which Compound (A) is combined with titanium chloride ($TiCl_4$), zinc, and tetrahydrofuran (THF) in a "McMurry Reaction" to form the alkene Compound (B). Compound (B) then undergoes a double-bond reduction/hydrogenation process at step 204 to form Compound (C) using a carbon-supported palladium catalyst and an ether solvent. Step 206 forms Compound (D) in a pyridine coupling reaction, which forms the biaryl linkage and results in acylation of the amines. At 208, the diacylated dihydropyridine Compound (D) is oxidized and the acyl groups are removed in a hydrolysis reaction to produce Compound (E). Amine alkylation is carried out at step 210 to form the Example Compound (I) having a hexanol functional group at each $R_1$ position.

The thus formed viologen-based compound of Example Compound (I) can be utilized as a cathodic component in an electrochromic medium for use in electro-optic elements and electrochromic devices as described herein.

The following non-limiting aspects are encompassed by the present disclosure. To the extent not already described, any one of the features of the following aspects may be combined in part or in whole with features of any one or more of the other aspects of the present disclosure to form additional aspects, even if such a combination is not explicitly described.

According to a first aspect of the present disclosure, an electro-optic element includes a low dimerizing electrochromic compound of Formula (I):

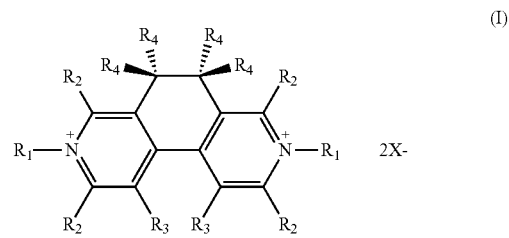

(I)

wherein:
  each $R_1$ is individually an alkyl, a hydroxyalkyl, or an alkyl substituted with at least one polymerizable functional group;
  each $R_2$ is a hydrogen;
  each $R_3$ is individually a hydrogen or an alkyl;
  each $R_4$ is individually a hydrogen, an alkyl, or a hydroxyalkyl; and
  $X^-$ is an anion.

The electro-optic element according to the first aspect, wherein the polymerizable functional group is selected from at least one of a vinyl group, acrylate group, methacrylate group, vinyl ether group, hydroxyl group, isocyanate group, oxetane group, and epoxy group.

The electro-optic element according to the first aspect or any intervening aspect, wherein each $R_4$ is a methyl group.

The electro-optic element according to the first aspect or any intervening aspect, wherein at least one $R_4$ includes a polymerizable functional group.

The electro-optic element according to the first aspect or any intervening aspect, wherein at least one $R_1$ includes a polymerizable functional group.

The electro-optic element according to the first aspect or any intervening aspect, wherein the electrochromic compound of Formula (I) is one of dissolved in a solvent, incorporated into a gel, or incorporated into a polymeric film.

The electro-optic element according to the first aspect or any intervening aspect, wherein the electrochromic compound of Formula (I) is at least one of incorporated into a backbone of polymeric chains forming the polymeric film or covalently bonded to polymeric chains of the polymeric film as a pendant group.

The electro-optic element according to the first aspect or any intervening aspect, wherein $X^-$ is selected from at least one of $F^-$, $Cl^-$, $Br^-$, $I^-$, $BF_4^-$, $PF_6^-$, $SbF_6^-$, $AsF_6^-$, $ClO_4^-$, $SO_3CF_3^{-1}$, $N(CN)_2^-$, $C(CF_3SO_2)_3^-$, $N(SO_2C_2F_5)_2^-$, $N(CF_3SO_2)_2^-$, and $Al(OC(CF_3)_3)_4^-$.

The electro-optic element according to the first aspect or any intervening aspect, further including an electrochromic medium including the electrochromic compound of Formula (I), and a chamber defined at least in part by a first conductive layer of a first substrate, a second conductive layer of a second substrate, and a sealing member joining the first substrate and the second substrate, wherein the electrochromic medium is disposed within the chamber.

According to a second aspect of the present disclosure, an electrochromic medium for use in an electro-optic element includes a low dimerizing electrochromic compound of Formula (I):

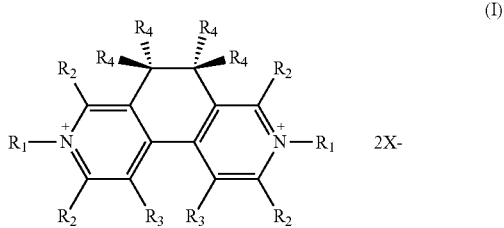

(I)

wherein:
  each $R_1$ is individually an alkyl, a hydroxyalkyl, or an alkyl substituted with at least one polymerizable functional group;
  each $R_2$ is a hydrogen;
  each $R_3$ is individually a hydrogen or an alkyl;
  each $R_4$ is individually a hydrogen, an alkyl, or a hydroxyalkyl; and
  $X^-$ is an anion.

The electrochromic medium according to the second aspect, wherein the polymerizable functional group is selected from at least one of a vinyl group, acrylate group, methacrylate group, vinyl ether group, hydroxyl group, isocyanate group, oxetane group, and epoxy group.

The electrochromic medium according to the second aspect or any intervening aspect, wherein each $R_4$ is a methyl group.

The electrochromic medium according to the second aspect or any intervening aspect, wherein at least one $R_4$ includes a polymerizable functional group.

The electro-optic element according to the first aspect or any intervening aspect, wherein at least one $R_1$ includes a polymerizable functional group.

The electrochromic medium according to the second aspect or any intervening aspect, wherein the electrochromic compound of Formula (I) is one of dissolved in a solvent, incorporated into a gel, or incorporated into a polymeric film.

The electrochromic medium according to the second aspect or any intervening aspect, wherein $X^-$ is selected from at least one of $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CN)_2^-$, $C(CF_3SO_2)_3^-$, $N(SO_2C_2F_5)_2^-$, $N(CF_3SO_2)_2^-$, and $Al(OC(CF_3)_3)_4^-$.

According to a third aspect of the present disclosure, an electro-optic element includes a low dimerizing electrochromic compound of Formula (II):

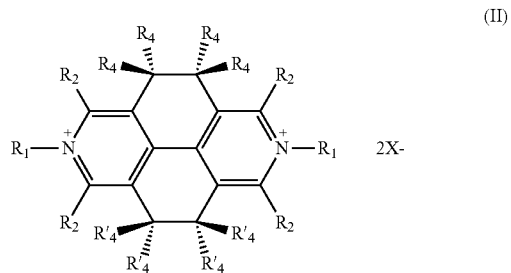

(II)

wherein:
  each $R_1$ is individually an alkyl, a hydroxyalkyl, or an alkyl substituted with at least one polymerizable functional group;
  each $R_2$ is a hydrogen;
  each $R_4$ is individually a hydrogen, an alkyl, or a hydroxyalkyl;
  each $R'_4$ is individually a hydrogen, an alkyl, or a hydroxyalkyl; and
  $X$ is an anion.

The electro-optic element according to the third aspect, wherein the polymerizable functional group is selected from at least one of a vinyl group, acrylate group, methacrylate group, vinyl ether group, hydroxyl group, isocyanate group, oxetane group, and epoxy group.

The electro-optic element according to the third aspect or any intervening aspect, wherein each $R_4$ and each $R'_4$ is a methyl group.

The electro-optic element according to the third aspect or any intervening aspect, wherein at least one $R_4$, at least one $R'_4$, or at least one $R_4$ and at least one $R'_4$ includes a polymerizable functional group.

The electro-optic element according to the first aspect or any intervening aspect, wherein at least one $R_1$ includes a polymerizable functional group.

The electro-optic element according to the third aspect or any intervening aspect, wherein the electrochromic compound of Formula (II) is one of dissolved in a solvent, incorporated into a gel, or incorporated into a polymeric film.

The electro-optic element according to the third aspect or any intervening aspect, wherein the electrochromic compound of Formula (II) is at least one of incorporated into a backbone of polymeric chains forming the polymeric film or covalently bonded to the polymeric chains of the polymeric film as a pendant group.

The electro-optic element according to the third aspect or any intervening aspect, wherein $X^-$ is selected from at least one of $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CN)_2^-$, $C(CF_3SO_2)_3^-$, $N(SO_2C_2F_5)_2^-$, $N(CF_3SO_2)_2^-$, and $Al(OC(CF_3)_3)_4^-$.

The electro-optic element according to the third aspect or any intervening aspect, further including an electrochromic medium including the electrochromic compound of Formula (II), and a chamber defined at least in part by a first conductive layer of a first substrate, a second conductive layer of a second substrate, and a sealing member joining the first substrate and the second substrate, wherein the electrochromic medium is disposed within the chamber.

According to a fourth aspect of the present disclosure, an electrochromic medium for use in an electro-optic element includes a low dimerizing electrochromic compound of Formula (II):

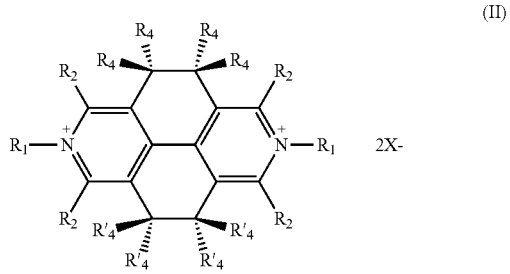

wherein:
each $R_1$ is individually an alkyl, a hydroxyalkyl, or an alkyl substituted with at least one polymerizable functional group;
each $R_2$ is a hydrogen;
each $R_3$ is individually a hydrogen or an alkyl;
each $R_4$ is individually a hydrogen, an alkyl, or a hydroxyalkyl;
each $R'_4$ is individually a hydrogen, an alkyl, or a hydroxyalkyl; and
$X^-$ is an anion.

The electrochromic medium according to the fourth aspect, wherein the polymerizable functional group is selected from at least one of a vinyl group, acrylate group, vinyl ether group, hydroxyl group, oxetane group, and epoxy group.

The electrochromic medium according to the fourth aspect or any intervening aspect, wherein each $R_4$ and each $R'_4$ is a methyl group.

The electrochromic medium according to the fourth aspect or any intervening aspect, wherein at least one $R_4$, at least one $R'_4$, or at least one $R_4$ and at least one $R'_4$ is a polymerizable functional group.

The electrochromic medium according to the fourth aspect or any intervening aspect, wherein the electrochromic compound of Formula (I) is one of dissolved in a solvent, incorporated into a gel, or incorporated into a polymeric film.

The electrochromic medium according to the fourth aspect or any intervening aspect, wherein $X^-$ is selected from at least one of $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CN)_2^-$, $C(CF_3SO_2)_3^-$, $N(SO_2C_2F_5)_2^-$, $N(CF_3SO_2)_2^-$, and $Al(OC(CF_3)_3)_4^-$.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:
1. An electro-optic element, comprising:
a low dimerizing electrochromic compound of Formula (I):

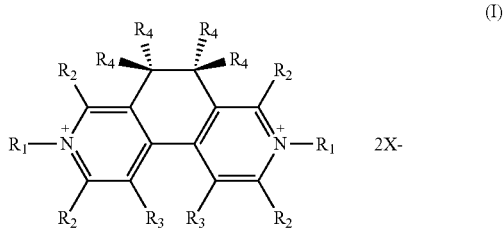

wherein:
each $R_1$ is individually an alkyl, a hydroxyalkyl, or an alkyl substituted with at least one polymerizable functional group;
each $R_2$ is a hydrogen;

each $R_3$ is individually a hydrogen or an alkyl;
each $R_4$ is individually a hydrogen, an alkyl, or a hydroxyalkyl; and
$X^-$ is an anion.

2. The electro-optic element of claim 1, wherein the polymerizable functional group is selected from at least one of a vinyl group, acrylate group, methacrylate group, vinyl ether group, hydroxyl group, isocyanate group, oxetane group, and epoxy group.

3. The electro-optic element of claim 1, wherein at least one $R_4$ is a methyl group.

4. The electro-optic element of claim 1, wherein the electrochromic compound of Formula (I) is one of dissolved in a solvent, incorporated into a gel, or incorporated into a polymeric film.

5. The electro-optic element of claim 4, wherein the electrochromic compound of Formula (I) is at least one of incorporated into a backbone of polymeric chains forming the polymeric film or covalently bonded to polymeric chains of the polymeric film as a pendant group.

6. The electro-optic element of claim 1, wherein $X^-$ is selected from at least one of $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CN)_2^-$, $C(CF_3SO_2)_3^-$, $N(SO_2C_2F_5)_2^-$, $N(CF_3SO_2)_2^-$, and $Al(OC(CF_3)_3l)_4^-$.

7. The electro-optic element of claim 1, further comprising:
an electrochromic medium comprising the electrochromic compound of Formula (I); and
a chamber defined at least in part by a first conductive layer of a first substrate, a second conductive layer of a second substrate, and a sealing member joining the first substrate and the second substrate,
wherein the electrochromic medium is disposed within the chamber.

8. An electrochromic medium for use in an electro-optic element, comprising:
a low dimerizing electrochromic compound of Formula (I):

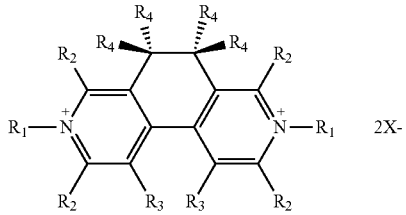

wherein:
each $R_1$ is individually an alkyl, a hydroxyalkyl, or an alkyl substituted with at least one polymerizable functional group;
each $R_2$ is a hydrogen;
each $R_3$ is individually a hydrogen or an alkyl;
each $R_4$ is individually a hydrogen, an alkyl, or a hydroxyalkyl; and
$X^-$ is an anion.

9. The electrochromic medium of claim 8, wherein the polymerizable functional group is selected from at least one of a vinyl group, acrylate group, methacrylate group, vinyl ether group, hydroxyl group, isocyanate group, oxetane group, and epoxy group.

10. The electrochromic medium of claim 8, wherein each $R_4$ is a methyl group.

11. The electrochromic medium of claim 8, wherein the electrochromic compound of Formula (I) is one of dissolved in a solvent, incorporated into a gel, or incorporated into a polymeric film.

12. The electrochromic medium of claim 8, wherein $X^-$ is selected from at least one of $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CN)_2^-$, $C(CF_3SO_2)_3^-$, $N(SO_2C_2F_5)_2^-$, $N(CF_3SO_2)_2^-$, and $Al(OC(CF_3)_3)_4^-$.

13. An electro-optic element, comprising:
a low dimerizing electrochromic compound of Formula (II):

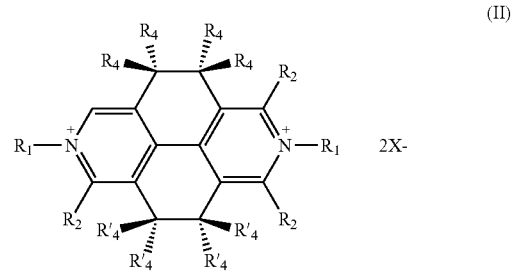

wherein:
each $R_1$ is individually an alkyl, a hydroxyalkyl, or an alkyl substituted with at least one polymerizable functional group;
each $R_2$ is a hydrogen;
each $R_4$ is individually a hydrogen, an alkyl, or a hydroxyalkyl;
each $R'_4$ is individually a hydrogen, an alkyl, or a hydroxyalkyl; and
$X^-$ is an anion.

14. The electro-optic element of claim 13, wherein the polymerizable functional group is selected from at least one of a vinyl group, acrylate group, methacrylate group, vinyl ether group, hydroxyl group, isocyanate group, oxetane group, and epoxy group.

15. The electro-optic element of claim 13, wherein at least one $R_4$ or at least one $R'_4$ is a methyl group.

16. The electro-optic element of claim 13, wherein the electrochromic compound of Formula (II) is one of dissolved in a solvent, incorporated into a gel, or incorporated into a polymeric film.

17. The electro-optic element of claim 13, wherein $X^-$ is selected from at least one of $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CN)_2^-$, $C(CF_3SO_2)_3^-$, $N(SO_2C_2F_5)_2^-$, $N(CF_3SO_2)_2^-$, and $Al(OC(CF_3)_3)_4^-$.

* * * * *

UNITED STATES PATENT AND TRADEMARK OFFICE
CERTIFICATE OF CORRECTION

PATENT NO. : 11,414,594 B2  
APPLICATION NO. : 16/841966  
DATED : August 16, 2022  
INVENTOR(S) : Kloeppner et al.

Page 1 of 1

It is certified that error appears in the above-identified patent and that said Letters Patent is hereby corrected as shown below:

In the Claims

Column 21, Claim 6, Line 24:  
"$Al(OC(CF_3)_3l\ )_4^-$." should be --$Al(OC(CF_3)_3)_4^-$.--; and Column 22, Claim 13, Line 25, Formula (II):

" 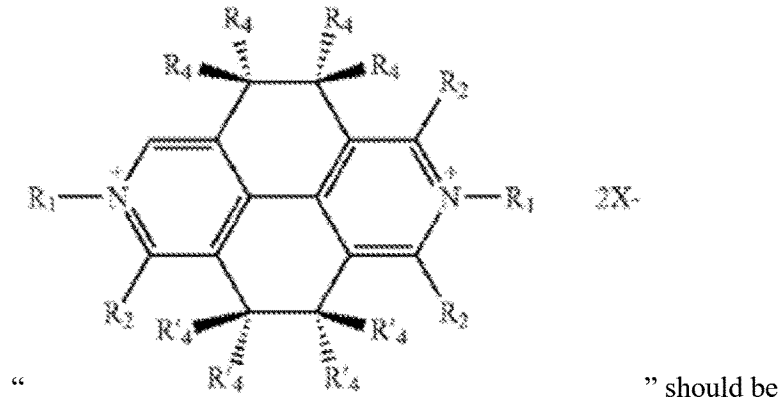 " should be

-- 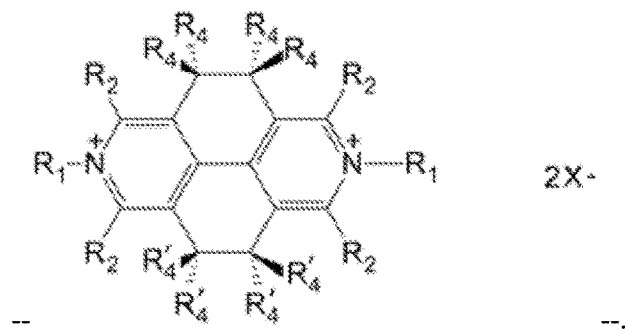 --.

Signed and Sealed this  
Twenty-fifth Day of October, 2022

*Katherine Kelly Vidal*

Katherine Kelly Vidal  
*Director of the United States Patent and Trademark Office*